US008696759B2

(12) United States Patent
Tong et al.

(10) Patent No.: US 8,696,759 B2
(45) Date of Patent: Apr. 15, 2014

(54) METHODS AND DEVICES FOR IMPLANTS WITH CALCIUM PHOSPHATE

(75) Inventors: Weidong Tong, Warsaw, IN (US); Larry Salvati, Goshen, IN (US); Pooja Kadambi, Cincinnati, OH (US)

(73) Assignee: Depuy Synthes Products, LLC, Raynham, MA (US)

( * ) Notice: Subject to any disclaimer, the term of this patent is extended or adjusted under 35 U.S.C. 154(b) by 520 days.

(21) Appl. No.: 12/424,049

(22) Filed: Apr. 15, 2009

(65) Prior Publication Data
US 2010/0268330 A1   Oct. 21, 2010

(51) Int. Cl.
*A61F 2/28*   (2006.01)

(52) U.S. Cl.
USPC ..................... 623/23.53; 427/2.26

(58) Field of Classification Search
USPC ........... 623/23.55–23.57; 427/2.1, 2.24, 2.26, 427/2.27, 307, 309
See application file for complete search history.

(56) References Cited

U.S. PATENT DOCUMENTS

| 2,711,364 | A | 6/1955 | Beach |
| 2,981,610 | A | 4/1961 | Snyder et al. |
| 3,106,499 | A | 10/1963 | Kendall |
| 3,108,931 | A | 10/1963 | Wendell |
| 3,844,859 | A | 10/1974 | Roni |
| 3,848,272 | A | 11/1974 | Noiles |
| 3,855,638 | A | 12/1974 | Pilliar |
| 3,960,741 | A | 6/1976 | Gabrail |
| 4,094,679 | A | 6/1978 | Washizawa et al. |
| 4,145,764 | A | 3/1979 | Suzuki et al. |
| 4,156,943 | A | 6/1979 | Collier |
| 4,206,516 | A | 6/1980 | Pilliar |
| 4,309,488 | A | 1/1982 | Heide et al. |
| 4,314,876 | A | 2/1982 | Kremer et al. |
| 4,330,891 | A | 5/1982 | Branemark et al. |

(Continued)

FOREIGN PATENT DOCUMENTS

| CA | 2108362 | 10/1992 |
| DE | 3409372 A1 | 9/1985 |

(Continued)

OTHER PUBLICATIONS

Beksac, B et al., "Surface finish mechanics explain different clinical survivorship of cemented femoral stems for total hip arthoplasty," J. Long-Term Effects Med. Implants 16(6):407-22 (2006).

(Continued)

*Primary Examiner* — David Isabella
*Assistant Examiner* — Ann Schillinger
(74) *Attorney, Agent, or Firm* — Nutter McClennen & Fish LLP

(57) ABSTRACT

Implants with a calcium phosphate containing layer are disclosed. The implants, which can have a metallic character (e.g., made from a cobalt chromium alloy), can include a surface that is exposed to one or more formulations that results in a chemical and/or physical modification. In some instances, the modified surface is texturized so as to include a plurality of surface pits. The average pit size opening can range, for example, from 40 nm to about 10 μm, and can include a plurality of average pit sizes in some cases. The modified surfaces can promote growth of a calcium phosphate layer, which can be accelerated relative to conventional techniques. Other variations of such implant surfaces, and methods of producing similar implant surfaces, are also discussed.

19 Claims, 12 Drawing Sheets

(56) References Cited

U.S. PATENT DOCUMENTS

| | | |
|---|---|---|
| 4,476,590 A * | 10/1984 | Scales et al. ............. 623/23.57 |
| 4,483,678 A | 11/1984 | Nishio et al. |
| 4,550,448 A | 11/1985 | Kenna |
| 4,554,050 A | 11/1985 | Minford et al. |
| 4,612,160 A | 9/1986 | Donlevy et al. |
| 4,678,523 A | 7/1987 | Sridhar et al. |
| 4,713,076 A | 12/1987 | Draenert |
| 4,746,532 A | 5/1988 | Suzuki et al. |
| 4,780,450 A | 10/1988 | Sauk et al. |
| 4,818,559 A | 4/1989 | Hama et al. |
| 4,846,837 A | 7/1989 | Kurze et al. |
| 4,955,911 A | 9/1990 | Frey et al. |
| 4,990,163 A | 2/1991 | Ducheyne et al. |
| 5,030,233 A | 7/1991 | Ducheyne |
| 5,068,122 A | 11/1991 | Kokubo et al. |
| 5,084,051 A | 1/1992 | Tormala et al. |
| 5,141,522 A | 8/1992 | Landi |
| 5,157,111 A | 10/1992 | Pachence |
| 5,171,273 A | 12/1992 | Silver et al. |
| 5,180,393 A | 1/1993 | Commarmond |
| 5,205,921 A | 4/1993 | Shirkanzadeh |
| 5,222,987 A | 6/1993 | Jones |
| 5,236,459 A | 8/1993 | Koch et al. |
| 5,258,029 A | 11/1993 | Chu et al. |
| 5,258,098 A | 11/1993 | Wagner et al. |
| 5,310,539 A | 5/1994 | Williams |
| 5,368,881 A | 11/1994 | Kelman et al. |
| 5,376,236 A | 12/1994 | Hanson et al. |
| 5,439,569 A | 8/1995 | Carpio |
| 5,456,723 A | 10/1995 | Steinemann et al. |
| 5,478,237 A | 12/1995 | Ishizawa |
| 5,508,267 A | 4/1996 | Czernuszka et al. |
| 5,543,441 A | 8/1996 | Rhee et al. |
| 5,545,262 A | 8/1996 | Hardee et al. |
| 5,571,188 A | 11/1996 | Ellingsen et al. |
| 5,573,771 A | 11/1996 | Geistlich et al. |
| 5,607,480 A | 3/1997 | Beaty |
| 5,658,333 A | 8/1997 | Kelman et al. |
| 5,681,310 A | 10/1997 | Yuan et al. |
| 5,705,082 A | 1/1998 | Hinson |
| 5,824,093 A | 10/1998 | Ray et al. |
| 5,826,586 A | 10/1998 | Mishra et al. |
| 5,843,172 A | 12/1998 | Yan |
| 5,843,289 A | 12/1998 | Lee et al. |
| 5,846,374 A | 12/1998 | Parab et al. |
| 5,855,612 A | 1/1999 | Ohthuki et al. |
| 5,876,453 A | 3/1999 | Beaty |
| 5,906,828 A | 5/1999 | Cima et al. |
| 5,947,893 A | 9/1999 | Agrawal et al. |
| 5,986,169 A | 11/1999 | Gjunter |
| 6,022,376 A | 2/2000 | Assell et al. |
| 6,031,148 A | 2/2000 | Hayes et al. |
| 6,033,582 A | 3/2000 | Lee et al. |
| 6,066,175 A | 5/2000 | Henderson et al. |
| 6,066,176 A | 5/2000 | Oshida |
| 6,069,295 A * | 5/2000 | Leitao ............. 623/11.11 |
| 6,077,076 A | 6/2000 | Comfort |
| 6,093,205 A | 7/2000 | McLeod et al. |
| 6,096,140 A | 8/2000 | Susa et al. |
| 6,113,640 A | 9/2000 | Tormala et al. |
| 6,121,172 A | 9/2000 | Marcolongo et al. |
| 6,136,369 A | 10/2000 | Leitao et al. |
| 6,143,948 A | 11/2000 | Leitao et al. |
| 6,146,686 A | 11/2000 | Leitao |
| 6,162,537 A | 12/2000 | Martin et al. |
| 6,179,872 B1 | 1/2001 | Bell et al. |
| 6,183,255 B1 | 2/2001 | Oshida |
| 6,187,461 B1 * | 2/2001 | Lin et al. ............. 428/832.1 |
| 6,207,218 B1 | 3/2001 | Layrolle et al. |
| 6,261,322 B1 | 7/2001 | Despres, III et al. |
| 6,299,596 B1 | 10/2001 | Ding |
| 6,319,286 B1 | 11/2001 | Fernandez et al. |
| 6,344,061 B1 | 2/2002 | Leitao et al. |
| 6,384,195 B1 | 5/2002 | Delgado et al. |
| 6,491,723 B1 | 12/2002 | Beaty |
| 6,569,489 B1 | 5/2003 | Li |
| 6,582,470 B1 | 6/2003 | Lee et al. |
| 6,749,766 B2 | 6/2004 | McLean et al. |
| 6,827,743 B2 | 12/2004 | Eisermann et al. |
| 7,041,164 B2 | 5/2006 | Kanca, III |
| 7,048,870 B1 | 5/2006 | Ellingsen et al. |
| 7,144,428 B2 * | 12/2006 | Anitua ............. 623/23.53 |
| 7,229,545 B2 | 6/2007 | Sewing et al. |
| 7,229,569 B1 | 6/2007 | Seki et al. |
| 7,285,229 B2 | 10/2007 | Kuriyama et al. |
| 7,368,065 B2 | 5/2008 | Yang et al. |
| 7,386,065 B2 | 6/2008 | Tu et al. |
| 7,501,073 B2 | 3/2009 | Wen et al. |
| 7,901,462 B2 | 3/2011 | Yang et al. |
| 2003/0065401 A1 | 4/2003 | Amrich et al. |
| 2003/0108659 A1 | 6/2003 | Bales et al. |
| 2003/0125808 A1 | 7/2003 | Hunter et al. |
| 2003/0130736 A1 | 7/2003 | Raab |
| 2003/0176927 A1 * | 9/2003 | Steinemann et al. ...... 623/23.55 |
| 2004/0121290 A1 | 6/2004 | Minevski et al. |
| 2004/0167632 A1 | 8/2004 | Wen et al. |
| 2004/0167633 A1 * | 8/2004 | Wen et al. ............. 623/23.57 |
| 2004/0199242 A1 | 10/2004 | Hong et al. |
| 2005/0043733 A1 | 2/2005 | Eisermann et al. |
| 2005/0049716 A1 | 3/2005 | Wagener et al. |
| 2005/0070989 A1 | 3/2005 | Lye et al. |
| 2005/0112397 A1 | 5/2005 | Rolfe et al. |
| 2005/0171604 A1 | 8/2005 | Michalow |
| 2005/0251260 A1 | 11/2005 | Gerber et al. |
| 2006/0018859 A1 | 1/2006 | Carter |
| 2006/0105015 A1 | 5/2006 | Perla et al. |
| 2006/0154206 A1 | 7/2006 | Petersson |
| 2006/0289388 A1 * | 12/2006 | Yang et al. ............. 216/96 |
| 2006/0293758 A1 | 12/2006 | Yang et al. |
| 2007/0260324 A1 | 11/2007 | Joshi et al. |
| 2008/0044449 A1 | 2/2008 | McKay |
| 2008/0081539 A1 | 4/2008 | Ernsberger |
| 2008/0241214 A1 | 10/2008 | Myung et al. |
| 2009/0005868 A1 | 1/2009 | Gundlapalli et al. |
| 2009/0008365 A1 | 1/2009 | Tong et al. |
| 2009/0175918 A1 | 7/2009 | Salvati et al. |
| 2009/0204213 A1 | 8/2009 | Liao et al. |
| 2009/0266791 A1 | 10/2009 | Yang et al. |
| 2010/0243429 A1 | 9/2010 | Aoki et al. |
| 2010/0268227 A1 | 10/2010 | Tong et al. |
| 2010/0268346 A1 | 10/2010 | Tong et al. |
| 2010/0268347 A1 | 10/2010 | Tong et al. |
| 2011/0190902 A1 | 8/2011 | Tong |

FOREIGN PATENT DOCUMENTS

| | | |
|---|---|---|
| DE | 3414924 A1 | 10/1985 |
| DE | 19504386 A1 | 8/1996 |
| DE | 19811900 A1 | 9/1999 |
| DE | 19812713 A1 | 9/1999 |
| DE | 19812714 A1 | 9/1999 |
| EP | 0389713 A1 | 10/1990 |
| EP | 0838286 A1 | 4/1998 |
| EP | 1674051 | 6/2006 |
| EP | 1 736 181 A1 | 12/2006 |
| EP | 1 736 182 A1 | 12/2006 |
| EP | 1962894 A2 | 9/2008 |
| EP | 2072629 | 6/2009 |
| EP | 2093311 | 8/2009 |
| GB | 2045083 A | 10/1980 |
| JP | 03-146679 B2 | 3/2001 |
| JP | 2002-535074 A | 10/2002 |
| JP | 2004-255183 A | 9/2004 |
| SU | 505 750 A1 | 3/1976 |
| WO | 9116012 A1 | 10/1991 |
| WO | WO-9203177 A1 | 3/1992 |
| WO | 92/05745 A1 | 4/1992 |
| WO | WO-9213984 A1 | 8/1992 |
| WO | WO-9218166 A1 | 10/1992 |
| WO | WO-9513101 A1 | 5/1995 |
| WO | WO-9817844 A1 | 4/1998 |
| WO | WO-9855053 A1 | 12/1998 |
| WO | WO-9930672 A2 | 6/1999 |
| WO | WO-9947082 A1 | 9/1999 |

(56) References Cited

FOREIGN PATENT DOCUMENTS

| WO | WO-9962439 A1 | 12/1999 |
|---|---|---|
| WO | 01/66479 A1 | 9/2001 |
| WO | 02/060507 A1 | 8/2002 |
| WO | WO-0267824 A2 | 9/2002 |
| WO | WO-02067824 A2 | 9/2002 |
| WO | 03/008657 A1 | 1/2003 |
| WO | 20041008984 A1 | 1/2004 |
| WO | 2005004941 A1 | 1/2005 |
| WO | WO-200767744 A2 | 6/2007 |
| WO | WO 2007/116690 | 10/2007 |
| WO | WO-2007116690 | 10/2007 |
| WO | 2009075095 A1 | 6/2009 |

OTHER PUBLICATIONS

Cheng, K. et al., "Osteolysis caused by tibial component debonding in total knee arthroplasty," Clin. Ortho.& Related Res. 443:333-36 (2006).
Conceicao, EN et al., "Chemical etching solutions for creating micromechanical retention in resin-bonded retainers," J. Pros. Denistry 71(3):303-09 (1994).
Crowninshield, R. et al., "Cemented femoral component surface finish mechanics," Clin. Ortho.& Related Res. 355:90-102 (1998).
Dowd, JE et al., "Failure of total hip arthroplasty with a precoated prosthesis," Clin. Ortho. & Related res. 355:123-36 (1998).
Han, HS et al., "High incidence of loosening of the femoral component in legacy posterior stabilized-flex total knee replacement," J. Bone Joint Surg. 89B:1457-61 (2007).
Mann et I., "Early cementing does not increase debond energy of grit blasted interfaces," J. Ortho. Res. 27:822-27 (2004).
Neto, HG et al., "Analysis of depth of the microporosity in a nickel-chromium system alloy—effects of electrolytic, chemical and sandblasting etching,"J. Oral Rehab. 30:556-58 (2003).
Anissian, H. et al., "Metal-on-Metal Bearing in hip Prosthesis Generates 100-fold Less Wear Debris than Metal-on-Polyethylene," Acta Orthopadica Scandanavica 70(6):578-82 (1999).
ASTM Designation: F 1537-00, "Standard Specification for Wrought Cobalt—28Chromium—6Molybdenum Alloys for Surgical Implants (UNS R31537, UNS R31538, and UNS R31539)," ASTM International (2003).
ASTM Designation: F 75-01, "Standard Specification for Cobalt—28 Chromium—6 Molybdenum Alloy Castings and Casting Alloy for Surgical Implants (UNS R30075)," ASTM International (2003).
Biomimetic Mineralization of Collagen by Combined Fibril Assembly and Calcium Phosphate Formulation, Jens-Hilmar Brat, et al. Chem. Mater. 1999, 11, 2694-2701.
Collagen-Hydroxyapitate Composties for Hard Tissue Repair, DA Wahl and Czernuszka, European Cells and Materials vol. 11 2006, 43-56.
Callaghan, "Ceramic-on-Polyethylene: Analysis of Results to Date", Seminars in Arthroplasty 14(2):86-88 (2003).
European Search Report from corresponding EP Appl. No. 10159874.6, dated Jul. 26, 2010.
European Search Report, from corresponding EP Appl. No. 09158913.5, dated Oct. 7, 2009.
Goldsmith, A. et al., "A Comparative Joint Simulator Study of the Wera of Metal-on-Metal and Alternative Material Combinations in Hip Replacements," Institution of Mech. eng., J. of Eng. In Med. 214:39-47 (2000).
Liao, Y-S et al., Effects of Clearance, Head Size and Start-Stop Protocol on Wear of Metalon-Metal Hip Joint Simulator, Ortho. Res. Soc., S.F., CA (2004).
U.S. Provisional Appl. No. 60/956,778, filed Aug. 20, 2007 to Salvati et al.
U.S. Appl. No. 12/696,880, filed Jan. 29, 2010 to Tong, et al.
[No Author Listed] "Passivation" from Wikipedia, downloaded on Dec. 2, 2008 at URLhttp://en.wikipedia.org/wiki/Passivation 3 pages.
Australian Office Action for application No. 2006-202728, issued Sep. 24, 2010. (2 pages).
Brady et al., "Chemistry: The Study of Matter and Its Changes", 1993, pp. 706-707, John Wiley & Sons, Inc.
Catledge, Journal of Nanoscience & Technology, vol. 2, No. 3, pp. 1-20, (2002).
Chinese Office Action for Application No. 200810144699.3, issued Mar. 17, 2011. (15 pages).
[No Author Listed] CRC Handbook of Metal Etchants, CRC Press, Boston, 315-316 (1991).
Dogliotti et al., "Flash photolysis of per[oxydi]sulfate ions in aqueous solutions. The sulfate and ozoned radical anions," J. Phys. Chem., 1967, 71(8), 2511-2516.
European Office Action and Search Report from corresponding EP Appl. No. 11151450.1, dated Sep. 20, 2011.
European Search Report for Application No. 06252690.0, issued Jul. 28, 2006. (8 pages).
European Search Report for Application No. 06252704.9, issued Jul. 28, 2006. (8 pages).
European Search Report for Application No. 08252311.9, issued Aug. 25, 2009. (13 pages).
Ferrari, Journal of Prosthetic Dentistry, vol. 62, pp. 516-521, (1989).
Japanese Office Action for Application No. 2006-172924, issued Feb. 22, 2011. (3 pages).
Japanese Office Action for Application No. 2006-172924, issued Nov. 8, 2011. (3 pages).
Japanese Office Action for Application No. 2006-172928, issued Feb. 22, 2011. (3 pages).
Japanese Office Action for Application No. 2006-172928, issued Feb. 28, 2011. (3 pages).
Jokela-Hietamaki, M. et al., "Resin Bond to Electrolytically Etched Cobalt-Chromium Alloys: Scandinavian J. Dental Res. 95(1):82 (1987)."
Kern, Handbook of Semiconductor Wafer Cleaning Technology, William Andrew Pub. (1993), pp. 120-128.
Liu et al., Surface modification of titanium, titanium alloys, and related materials for biomedical applications. Mater Sci Engin. Dec 4, 2004;47(3-4):49-121.
Liu, L. et al., "Etched Casting Resin Bonded Bridge: The Laboratory Study of Electrolytic Etchina of a Co-Cr Alloy," Chinese Oral Med. J. 22(5):287 (Chinese, English @ 311)(1987).
Mendelson, Journal of Applied Physics, vol. 32, pp. 1579-1583, (1961).
Nabadalung, D. et al., Effectiveness of Adhesive Systems for a Co-Cr Removable Partial Denture Alloy: J. Prosthodontics 7(1):17 (1998).
Petzow, G. et al., Metallographic Etching, Am. Soc. For Metals, Ohio 51 (1978).
Reclaru, L. et al., "Cobalt-Chromium Dental Alloys Enriched with Precious Metals," European Cells & Materials 7 (Supp. 2):51 (2004).
[No. Author Listed] Research Discloser 293054, Process to enhance the adhesion of a polymer film to a steel alloy surface, Sep. 1988, p. 1-2.
Sarac, Y. et al., The Effects of Different Metal Surface Treatments on Marginal Microleakage in Resin-Bonded Restorations-Tr. J. of Medical Sciences 28:685 (1998).
Wolf, Silicon Processing for the VLSI Era, vol. 1, Lattice press (1986), p. 518.
Becker et al., "Proliferation and Differentiation of Rat Calvarial Osteoblasts on Type I Collagen-Coated Titanium Alloy," J. Biomed. Mater. Res. 59(3):516-27 (2002).
Coyle, T.W. et al., "Plasma Spray Deposition of Hydroxyapatite Coatings From Sol Precursors," Mat. Sci. Forum vols. 539-543 (2007) online at http://www.scientific.net.
De Groot, K. et al., "New Biomimetic HA Coatings," Phosphorous Res. Bull. 6:71-74 (1996).
DePuy Spine, Inc., Helos Bone Graft Replacement, http://www.depuyspine.com/products/biologicsolutions/helos.asp, Nov. 20, 2013.
Extracellular Matrix (ECM), http://web.indstate.edu/theme/mwking/extracellularmatrix.html (Jan. 24, 2008).
Hydroxylapatite, http://en.wikipedia.org/wiki/Hydroxylapatite, Nov. 23, 2013.
Kim, et al., "Preparation of Bioactive Ti and its Alloys Via Simple Chemical Surface Treatment," J. Biomed. Mat. Res. 32:409-17 (1996).

(56) References Cited

OTHER PUBLICATIONS

Kokubo, T. et al., "Spontaneous Formation of Bonelike Apatite Layer on Chemically Treated Titanium Metals," J. Am. Ceram. Soc. 79(4):1127-29 (1996).

Leitao, E. et al., "In Vitro Calcification of Orthopedic Implant Materials," J. Mat. Sci. 6(12):849-52 (Dec. 1995).

Leitao, E. et al., "Influence of Substrate Material and Surface Finishing on the Morphology of the Calcium-Phosphate Coating," J. Biomed. Mat. Res. 36:85-90 (1997).

Leitao, E., "Surface Modifications of Biomaterials vs. Biological Behavior," Univ. of Oporto (1996).

LifeNet Health, Safe and Effective Osteobiologic Options, www.accesslifenet.org/allograft_bio-implants/?family=1, 2013.

Pasteris, J. et al., "Apatite in Bone is Not Hydroxylapatite: There Must be a Reason," GSA Annual Meeting, Nov. 5-8, 2001, Paper 158-0, http://gsa.confex.com/gsa/2001AM/finalprogram/abstract_23719.htm.

Porocoat Porous Coating: For Use in Cementless Joint Replacement Surgery, Joint Replacement.com Restoring the Joy of Motion, http://www.jointreplacement.com/xq/ASP.default/pg.content/content_id.294/qx/default.htm, 2013.

Svehla et al., "No Effect of a Type I Collagen Gel Coating in Uncemented Implant Fixation," J. Biomed. Mater. Res. B Appl. Biomater. 74(1):423-28 (Jul. 2005).

Tanahashi, M. et al., Apatite Coating on Organic Polymers by a Biomimetic Process, J. Am. Ceram. Soc. &&(11):2805-08 (1994).

\* cited by examiner

METHODS AND DEVICES FOR IMPLANTS WITH CALCIUM PHOSPHATE

CROSS REFERENCE TO RELATED APPLICATIONS

The present application is related to the following three applications, which are all filed on the same day: (i) U.S. patent application Ser. No. 12/754,290, entitled "Micro and Nano Scale Surface Textured Titanium-Containing Articles and Methods of Producing Same," having inventors Weidong Tong and Larry Salvati; (ii) U.S. patent application Ser. No. 12/754,340, entitled "Nanotextured Cobalt-Chromium Alloy Articles having High Wettability and Method of Producing Same," having inventors Weidong Tong and Larry Salvati; and (iii) U.S. patent application Ser. No. 12/424,000, entitled "Methods and Devices for Bone Attachment," having inventors Weidong Tong and Larry Salvati. All three of these applications are hereby incorporated herein by reference in their entirety.

FIELD OF THE APPLICATION

The technical field of the present application is directed generally to manufactured substrates, and particularly to modifying such substrates to improve their characteristics for use as portions of a medical implant.

BACKGROUND

Medical implants for use as replacement structures in patients have become widespread in their application. In particular, orthopaedic implants for replacing joints or other structures have received a great deal of attention commercially and scientifically. Oftentimes, orthopaedic implants have a porous metallic surface, which is situated adjacent to bone.

Promotion of early implant fixation, in lieu of cement or other adhesives, and growth of bone to the implant are important considerations. Fixation proceeds by bone growth from the host bone toward the implant surface, which can typically begin about three weeks after the implant is inserted into a recipient. Progressive stabilization of the implant is achieved once the new bone bridges the gap between the implant surface and the original adjacent bone surface. Thus, to improve implant fixation, it can be advantageous to develop new methods and materials that can help promote bone attachment to non-cemented implants by, for example, promoting new bone growth.

SUMMARY

Some exemplary embodiments are drawn toward methods for preparing a surface of an implant. Such preparations can improve calcium phosphate coating of the implant in some instances. A metallic substrate can be exposed to a first formulation to impart a first chemically modified, texturized surface to the metallic substrate. In some instances, a second formulation can also be exposed to the metallic substrate to form a second chemically modified, texturized surface on the metallic substrate. When multiple different formulations are applied, each formulation can provide a distinct modification (e.g., one formulation etching larger scale features while another formulation etches small scale features). While the formulations can be applied in any order, in some instances the formulation used to form smaller features is applied after the formulation used to form larger features.

The metallic substrate used with some embodiments can be made of a metallic alloy suitable for implantation in a living being. Examples include titanium alloy and chromium containing alloys, such as a cobalt chromium alloy. In some embodiments, the metallic substrate, before surface modification, can include a porous structure (e.g., having a characteristic length greater than about 50 µm), which can be located on a surface of the implant. The porous surface can be made by pretreating a material using one or more mechanical roughening techniques, and/or applying a plurality of elements (e.g., cobalt chromium alloy elements) on a substrate surface to form the porous structure. Other pretreatments can be applied to a substrate surface prior to modification, such as plasma treatment using oxygen and/or argon.

The formulation(s) used to impart the modified surface can be any suitable to achieve the desired modification. In some embodiments, a formulation includes a hydrohalic acid. Hydrohalic acid formulations can also include an oxidant, which can impart a microtexture to a surface (e.g., surface pits with an average opening size from about 200 nm to about 10 µm). Other formulations including a hydrohalic acid can substantially exclude the presence of an oxidant, which can impart a nanotexture to a surface (e.g., surface pits with an average opening size from about 40 nm to about 200 nm). A surface can be exposed to one or more of the formulations for a time period of about 2 minutes to about 24 hours, or about 2 minutes to about 120 minutes, or for a time period longer than about 5 minutes.

The modified surface formed by exposure to the one or more formulations can be characterized by a plurality of surface pits. The surface pits can exhibit one or more characteristics such as an average opening size. The average opening size formed by any particular formulation can range from about 40 nm to about 10 µm; or from about 40 nm to about 200 nm; or from about 200 nm to about 10 µm. The surface pits can also be characterized by an average pit depth, which can be, for example, in a range from about 5 nm to about 500 nm, or from about 5 nm to about 50 nm, or from about 50 nm to about 500 nm. The modified surface can also, or alternatively, exhibit an enhanced chromium to cobalt ratio in at least a portion of a surface layer (e.g., within about 25 angstroms of the surface) relative to a cobalt-chromium alloy not being exposed to one of the modifying formulations.

In other embodiments, the metallic substrate can be treated with a formulation to form a calcium phosphate containing layer on the modified surface. The calcium phosphate containing layer can include hydroxyapatite, and/or can be biomimetic by including other ions. The layer can have an average thickness that is greater than about 100 nm (e.g., in a thickness range between about 1 µm and about 30 µm. Formulations can include fluid based mixtures with calcium and phosphate. Accordingly, the mixtures can provide a calcium phosphate layer that contacts a porous surface beyond a line-of-sight perspective, e.g., substantially covering the entire exposed surface. In some embodiments, the calcium phosphate containing layer can be formed after a time period of less than about 24 hours.

Further embodiments are directed to calcium phosphate coated implants that can include a metallic surface such as a cobalt chromium alloy surface. The metallic substrate can include a texturized surface having a plurality of surface pits, which can be characterized by any of the properties disclosed herein. A calcium phosphate layer can contact at least a portion of the texturized surface, the layer also exhibiting any of the corresponding properties disclosed herein.

BRIEF DESCRIPTION OF THE DRAWINGS

Aspects of the present invention will be more fully understood from the following detailed description taken in conjunction with the accompanying drawings (not necessarily drawn to scale), in which.

DETAILED DESCRIPTION OF EMBODIMENTS

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Embodiments of the present invention can be directed to devices and methods of forming implants, which can be inserted into a subject to act as a structural replacement (e.g., a joint replacement). Such implants can have a modified surface, e.g., relative to a substrate surface, which can promote the fixation of a calcium phosphate material in vitro that subsequently improve bone fixation to the implant. In some instances, the modified surface can be a modified metallic surface (e.g., cobalt-chromium alloy surface), which can be chemically and/or physically modified to promote calcium phosphate material fixation thereon. A calcium phosphate layer can be added to the modified surface. As discussed in further depth herein, the techniques and structures disclosed can provide potential advantages over the prior art such as improving bone attachment to the implant, improving a calcium phosphate containing material's ability to attach to the implant, and/or improving the efficiency by which such devices can be manufactured.

Implants with Modified Surfaces

Figure 1:
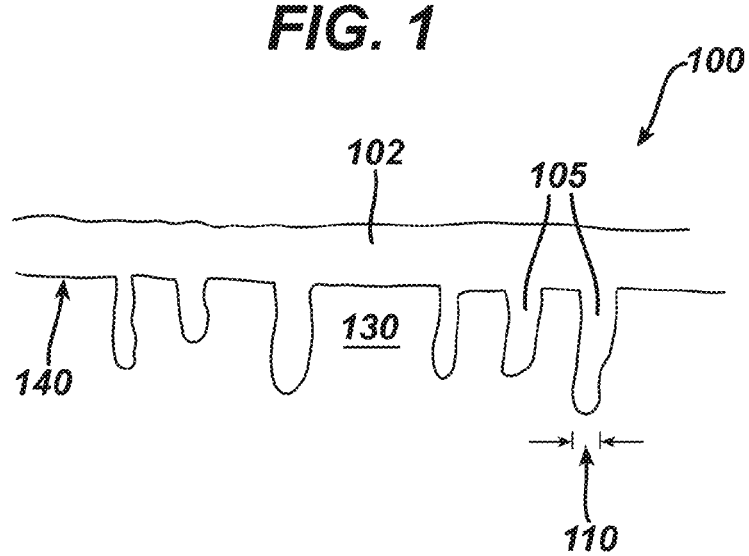
FIG. 1 is schematic diagram of a texturized surface, consistent with some embodiments.
Figure 2:
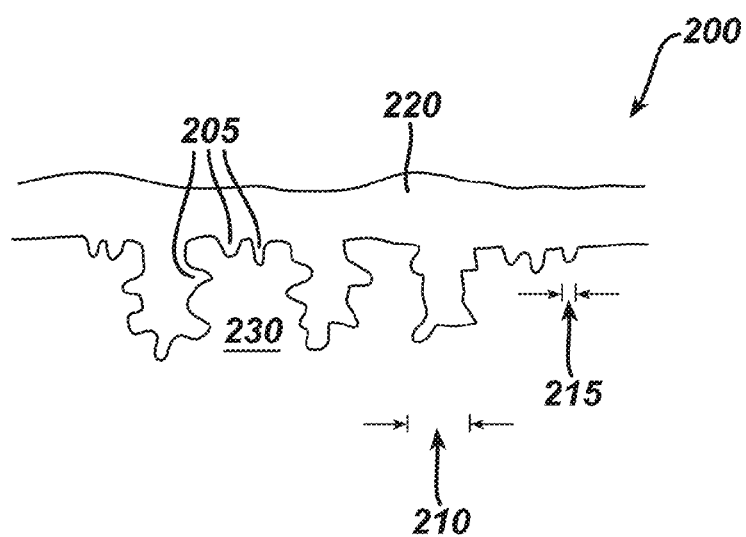
FIG. 2 is a schematic diagram of a multitexturized surface, in accord with some embodiments.

Some exemplary embodiments of the invention are described with reference to a schematic of an implant, such as shown in FIGS. 1 and 2. A section of the implant includes a modified surface, which can be configured to face a bone section upon implantation in a subject. With reference to FIG. 1, the implant 100 can have a modified surface 140 relative to the properties of the surface of an underlying native substrate 130. In some instances, the modified surface can be modified chemically, physically, or in both manners. Such alterations can act to promote the formation of a calcium phosphate material 120 on the modified surface 140, and or promote bone fixation of the implant structure 100.

The composition of the substrate and/or the surfaces of the substrate can be anything suitably consistent with the embodiments described herein. Materials such as metals, ceramics, polymers, and other materials, including composites of materials, can be utilized. In some embodiments, the surfaces of the substrate can be metallic. In general, the term "metallic" is used to describe an object having at least some qualities of bulk metals. Accordingly, metallic surfaces and substrates exhibit at least one property similar to that of bulk metals. For example, non-metallic materials that have trace contaminants of metal impurities can be excluded from a description of metallic surfaces and substrates. Exemplary metallic materials used for implants can include those suitable for medical implantation within a subject, such as titanium-based materials, titanium-based alloys (e.g., Ti6Al4V), and chromium-based alloys (e.g., a cobalt-chromium alloy or a cobalt-chromium-molybdenum alloy). Examples of cobalt-chromium alloys include alloys consistent with ASTM standard F 1537-00 and F 75-01, and cobalt chromium molybdenum alloys having substantially higher than about 25% chromium (e.g., chromium in a range from about 26% to about 30%) and higher than about 3% molybdenum (e.g., molybdenum in a range from about 5% to about 7%).

The surface of a substrate before modification can have any number of morphologies including flat, polished, irregular, and porous. Irregular or porous surfaces can be formed by using mechanical techniques to provide surface features that are larger than about 50 µm on average (e.g., pore spacing). Such features can be formed using mechanical methods, such as grit blasting and/or surface abrading and/or appropriate chemical methods, which can be consistent with techniques known to one skilled in the art. Accordingly, in some embodiments, a texturized surface can be overlaid on a previously prepared substrate surface exhibiting these larger surface features.

Porous networks on surfaces are utilized in some embodiments, which can be subsequently modified using one or more of the techniques disclosed herein. The porous network of a substrate can generally be embodied in a variety of sizes and geometries. In some embodiments, the porous network comprises a three-dimensional network, i.e., the pores of the network can be directed in any dimension. Such networks can have a variety of structures (e.g., open and/or closed cell), and can be formed by a variety of methods, such as etching of a substrate surface with a chemical and/or mechanical technique. In some embodiments, a plurality of elements can be used to form a porous network on a substrate surface. Such elements can be made from any materials (e.g., a chromium containing material such as a cobalt chromium alloy), though in some embodiments the elements are made from a metallic material, which can be similar in nature to the native surface of a substrate to which the elements are to be attached. The plurality of elements can be a variety of objects such as particulates, meshes, wires, other elemental structures, and combinations of such elements. In some embodiments, the elements are sized such that one, two, or three dimensions of the element exhibit an average size in the range of about 10 μm to about 1 mm. For example, particulates, such as beads or irregularly shaped particulates, can be utilized with an average effective diameter of about 250 μm. The average effective diameter of an irregularly shaped particle can be determined using any of the methods known to one skilled in the art including methods yielding a value independent of determining the precise size of each particulate (e.g., adsorption isotherms). In other embodiments, the elements are arranged so that the porous network has a depth of at least about two times the average smallest dimension of the elements comprising the network. For example, beads can be distributed on a substrate to form a porous surface in which the depth of the beads is at least about 3 times the average bead diameter. One particular example includes the use of Porocoat® Porous Coating beads made of a cobalt-chromium alloy to form a porous network. The porous network can also be integrally formed with the substrate, e.g., being a section of trabecularized metal.

The implants disclosed herein can have physically modified surfaces that are characterized in a variety of manners. In some embodiments, the physical modification is exhibited as a texturized surface. The texturized surface can be characterized in a variety of manners, for example by the formation of a plurality of surface pits 105 on the modified surface 140 as shown in FIG. 1. The surface pits can be characterized in a variety of manners as well. For example, the surface pits can be characterized by an average opening size 110, as depicted in FIG. 1 for example. The range of average size opening can vary, for example being in a range from about 40 nm to about 10 μm; or about 200 nm to about 10 μm, or about 40 nm to about 200 nm.

The average size opening refers to the average characteristic length scale of a selected set of surface pit openings. If all the surface openings are perfectly circular, the average size opening is the average diameter of the openings. When the surface openings are not uniform in geometry, the average size opening can have a value as understood by those skilled in the art. For instance, the average size opening can be the average effective diameter of the size openings (e.g., the average of twice the square root of the quantity of the area of an opening divided by pi).

Measurement of one or more surface characteristics to derive the size of a pit opening or other physical surface aspect (e.g., roughness, pit depth, surface area, etc.) can be achieved using any of the techniques known to one skilled in the art. In some instances, the surface pit can be characterized by using images obtained from techniques such as transmission electron microscopy or scanning electron microscopy. The images can be analyzed using conventional image analysis to obtain sizes such as pit opening dimensions. Other techniques can also be used such as atomic force microscopy, also known as scanning force microscopy.

In some embodiments, a texturized surface can be characterized as a multitextured surface. Such a multitextured surface can be the result of one or more processes, where the processes can impart a plurality of distinct average surface pit sizes to a substrate (e.g., a histogram of surface pit sizes would reveal a multimodal distribution). An example of a multitexturized surface is depicted in FIG. 2. The implant 200 has a substrate 230 (e.g., a metallic substrate such as a titanium alloy or a cobalt-chromium alloy) with surface pits 205 that can be characterized by two or more distinct average surface pit opening sizes. In some instances, the smaller average pit opening size 215 (e.g., having an average size smaller than 200 nm and/or larger than about 40 nm) can be overlaid the larger average pit opening sizes 210 (e.g., having an average size larger than about 200 nm and/or smaller than about 10 μm).

As documented by some of the experiments disclosed herein, the use of a modified surface can surprisingly lead to enhanced deposition of a calcium phosphate containing material 220. For instance, multitextured surfaces can lead to enhanced rates of calcium phosphate containing material deposition relative to the use of a textured surface characterized by any single average surface pit opening size. In some embodiments, surfaces with lower effective surface areas can exhibit enhanced deposition rates of calcium phosphate containing materials relative to surfaces with higher effective surface areas. Without being bound to any particular theory, such enhanced depositing is not necessarily easily explained as purely a function of surface area enlargement. For instance, nanotextured surface can exhibit lower surface areas than microetched surfaces due to the smaller depths of the corresponding pits. However, the nanotextured surfaces may provide a larger number of nucleation sites for precipitation per unit surface area due to the nanostructured features. Accordingly, the use of microtexturing to increase surface area, and nanotexturing to increase nucleation sites, may combine to stimulate enhanced calcium phosphate growth. In general, it is clear that one skilled in the art cannot predictably explain the enhancement in calcium phosphate loading rates, especially without the results presented in the present application.

While the surface pits described herein often times are characterized by one or more average opening sizes, it is understood that the pits can also be characterized by other pit measures including those understood by the skilled artisan. Examples include pit depths. For instance, the average pit depth can be in a range from about 5 nm to about 500 nm; or about 5 nm to about 50 nm; or about 50 nm to about 500 nm. Average depth sizes can be defined and measured using techniques as described herein with respect to average pit opening sizes, which can be consistent with the understanding of one skilled in the art.

Other examples of texturized surface characterization can include measures of roughness such as $R_a$, $R_q$, $R_{max}$, enhancement of surface area relative to a perfectly flat surface, or any combination of such. For example, some surfaces can be characterized by a $R_a$ or $R_q$ value larger than about 9 nm or about 60 nm, about 80 nm; and/or smaller than about 30 nm or about 110 nm or about 140 nm. It is understood that multiple characterizations can also be used to define texturized surfaces, where the combination of characterizations can include any combination of characteristics disclosed herein, which are consistent with one or more of the embodiments.

With respect to chemical modifications, implants consistent with at least some of the embodiments herein can include surface changes, which can potentially promote development of a calcium phosphate material thereon or other properties. Chemical modifications can be embodied in any number of manners, which can depend on the formulation used to create a chemical modification. For instance, in some embodiments, the chemical modification can result in an enhancement of one or more components in a surface layer relative to an unmodified native surface layer. In some particular embodiments, the surface modification can enhance the chromium fraction in a surface layer of the modified surface relative to the chromium fraction in a native surface of a metallic material such as a cobalt-chromium alloy. For example, the chromium to cobalt ratio in at least a portion of a surface layer of a modified surface can be higher than the chromium to cobalt ratio in the comparative portion of an unmodified surface layer. The layer of the modified surface can be in a region extending from the surface to a given depth, which can be up to about 10 to about 30 angstroms. Such chromium enhancement can homogenize a surface layer chemical composition; enhance the surface wettability; and/or improve chemical degradation properties with increased chromium oxide thickness. Enhancement of one component's presence relative to another can be achieved in any number of ways, for instance by depleting a particular component's presence (e.g., depleting cobalt in a layer to effect a net increase in the Cr/Co ratio). While some chemical modifications are explicitly disclosed herein, the scope of the invention is not to be limited to these disclosures. Other chemical modifications are also contemplated, including those inherent in some of the processes disclosed herein and/or known to those skilled in the art.

When calcium phosphate containing materials are used in some embodiments, such materials can include a variety of forms of calcium phosphate suitable for implantation within a living being. Calcium phosphate containing materials typically contain calcium phosphate in an amount above a typical trace amount equivalent to contamination. Accordingly, the amount of calcium phosphate can be greater than about 0.01%, 0.1%, 1%, 5%, or 10%.

In some embodiments, the calcium-phosphate containing material can include apatite. For instance, the apatite can include compounds of the formula: $Ca_5(PO_4)_3$ (OH, F, Cl or $CO_3$). Other non-limiting examples of other suitable biocompatible calcium-phosphate containing materials include: hydroxyapatite, alpha-tricalcium phosphate, beta-tricalcium phosphate, polymorphs of calcium phosphate, and combinations of such materials. In accordance with some embodiments, the calcium phosphate containing material includes hydroxyapatite.

Calcium phosphate containing material can also include various other component(s). For instances, one or more salts or other materials in a variety of amounts can be added. In some embodiments, the one or more salts can have a profile similar to a biological substance in a subject (e.g., blood, biological fluid, bone, etc.). Examples of ions include calcium, various phosphates (e.g., $HPO_4^{-2}$, $H_2PO_4^{-1}$), various carbonate ions (e.g., $HCO_3^{-1}$), magnesium, sodium, potassium, chlorine, sulfates, and silicates. Adsorbed species such as water and gases (e.g., $CO_2$) can also be present. Another potential component can be Tris(hydroxymethyl)aminomethane, which can be added to control the pH of a coating solution.

In some embodiments, the calcium-phosphate containing material is distributed in the pits of a modified surface, and can adhere to the modified surface. The material can form a layer thereon, which can have a variety of non-limiting thicknesses. In some instances, the thickness is in a range between about 1 μm and/or an upper limit that can be about 5, 10, 20, 30, 40, 50, or 100 μm. As well, in some embodiments, the coating can extend beyond a line-of-sight perspective, e.g., the exterior surface of a porous material can be substantially covered in all directions.

It is understood that structures consistent with the embodiments disclosed herein only represent some embodiments of the present invention. Indeed, any permutation and combination of the features as disclosed in FIGS. 1 and 2, and other figures and description in the present application, can be assembled to practice an embodiment consistent with some aspects of the present invention. Other embodiments can include other features, or present modification(s) and/or variation(s) to the features of the embodiments of FIGS. 1 and 2. Some of the aspects of the embodiments of FIGS. 1 and 2 are elaborated in further detail herein. Any number of the aspects discussed with respect to an element can be assembled with other elements, or practiced individually, consistent with the scope of the present invention.

Methods of Forming Implant Surfaces

Some embodiments of the present invention are drawn toward methods of preparing surfaces of an implant. Such methods can aid in the development of a layer of calcium phosphate material on the implant, which can aid bone adhesion to the implant upon the insertion of the implant in a subject's body. For instance, a method can provide a modified surface (e.g., chemically-modified, physically modified, or both) relative to a native substrate surface that promotes precipitation on the modified surface. The method can optionally include depositing a layer of calcium phosphate containing material on the modified surface. In some embodiments, such methods can yield an implant consistent with the embodiments disclosed herein. It is understood, however, that some of these methods can be used to produce other structures and devices extending beyond the explicitly described implants in the present application, and thus the methods are not necessarily limited to producing such implants.

Figure 3:
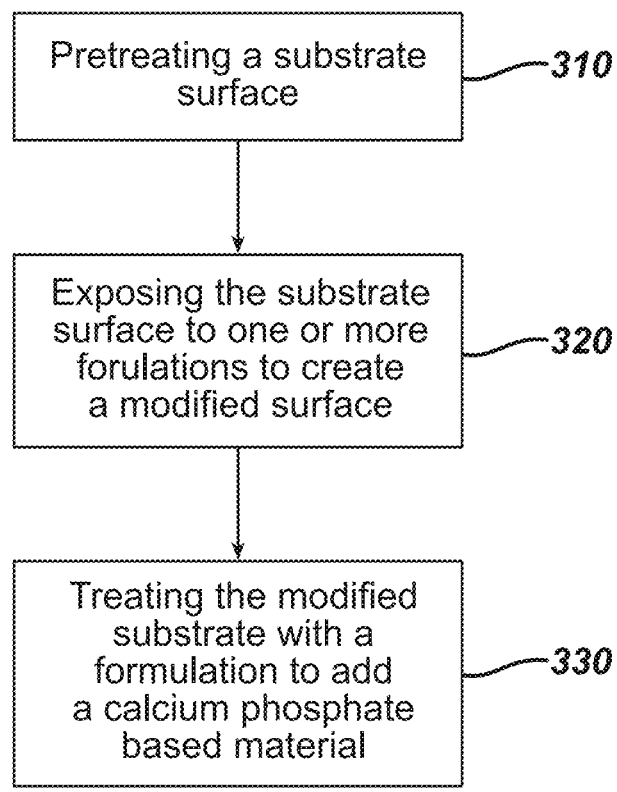
FIG. 3 presents a flow chart depicting a process for preparing a surface of an implant, consistent with some embodiments.

The flow diagram of FIG. 3 presents some embodiments of methods that can be used to prepare implants. A process can include a step of pretreating a substrate surface 310, which can be performed before modifying the substrate surface. The one or more pretreatments that can be employed include any number of steps that can prepare a surface for modification. Non-limiting examples include mechanical treatments such as grit-blasting and/or mechanical abrasion with solid and/or liquid mixtures. Such treatments can form features having an average macroscopic characteristic size on the substrate surface (e.g., an average feature size larger than about 50 μm). Appropriate chemical techniques can be used in addition, or alternatively, as understood by those skilled in the art.

Pretreatments can also be employed to create a porous surface of a substrate, for example by mechanical and/or chemical techniques that alter a substrate surface to cause removal of material from the surface resulting in a porous structure having the desired characteristics. Porous surfaces can also be created by placing discrete elements (e.g., having a smallest characteristic dimension from about 10 μm to about 1 mm) on the substrate surface to form the porous surface. The elements can have a variety of shapes and sizes, as previously described herein, and can be deposited on a surface to form the porous network (e.g., a three-dimensional porous network). Such elements can be adhered to the surface using any appropriate technique, including those known to one skilled in the art (e.g., using an adhesive and/or heat treating/sintering).

Another pretreatment can include exposing a metallic substrate surface to a plasma. For instance, plasmas containing oxygen and/or argon can be used increase the ratio of chromium to cobalt in a surface relative to an untreated surface (e.g., in a layer within about 25 angstroms of the surface). Such enrichment can be consistent with any of the embodiments disclosed herein. Further details regarding plasma treatments are available in a pending U.S. patent application bearing Ser. No. 12/110,404, filed Apr. 28, 2008, entitled "Implant Surfaces and Treatments for Wear Reduction," which is hereby incorporated herein by reference in its entirety.

A substrate surface can be exposed to one or more treatment formulations to create a modified surface 320 on the substrate. Exposure to the one or more formulations can modify a surface physically, chemically, or in both manners, which can be consistent with any of the properties discussed herein. In some embodiments, these formulations can be chosen to impart such characteristics based upon the nature of the substrate surface exposed. For example, the formulations can be specially tailored to impart chemical/mechanical characteristics to metallic substrates, which can be titanium alloys and/or chromium-based alloys.

Some particular embodiments are drawn to utilize formulations that can create a microetch-morphology on a metallic surface. For instance, the formulation can create a plurality of pits on a titanium alloy or cobalt-chromium alloy surface having an average pit opening size larger than about 200 nm or about 500 nm, and/or smaller than about 10 µm or about 5 µm, or about 1 µm. The pits can also, or alternatively, exhibit an average depth as disclosed in embodiments described herein, e.g., an average depth in a range from about 50 nm to about 500 nm. Such formulations can utilize any appropriate composition capable of achieving the described substrate structure. Some embodiments of the formulation are described in U.S. Pat. No. 7,368,065, which is incorporated herein by reference it its entirety.

In other embodiments, a formulation can create a modified surface having a nanoetch morphology. For instance, the formulation can create a plurality of pits on a titanium alloy or cobalt-chromium alloy surface having an average pit opening size larger than about 40 nm, about 50 nm, or 60 nm, and/or smaller than about 200 nm, or about 150 nm, or about 100 nm. The pits can also, or alternatively, exhibit an average depth as disclosed in embodiments described herein, e.g., an average depth in a range from about 5 nm to about 50 nm. Any type of formulation capable of providing such a structure can be utilized. A description of such formulations is provided in two U.S. Patent Applications that are filed concurrently on the same day with the present application: (i) a U.S. patent application Ser. No. 12/754,290 entitled "Micro and Nano-scale Surface Textured Titanium-Containing Articles and Methods of Producing Same," having inventors Weidong Tong and Larry Salvati; and (ii) a U.S. patent application Ser. No. 12/754,340 entitled "Nanotextured Cobalt Chromium Alloy Articles and Method of Producing Same," having inventors Weidong Tong and Larry Salvati. Both these application are hereby incorporated by reference in their entirety.

Alternative embodiments can utilize multiple formulations that can be applied in series to create a modified surface. The formulations can be applied in any appropriate sequence. For instance, a process can expose a substrate to a microtexturing formulation followed by a nanotexturing formulation. These serially applied formulations can lead to a multitextured surface, which can be associated with various advantages as discussed herein.

In particular embodiments, the formulations used to provide surface modification can include a hydrohalic acid, for instance a hydrohalic acid that substantially excludes hydrofluoric acid. As well, such formulations can also be substantially free of other potentially hazardous components such as aqua regia and/or methanol. In some embodiments, such as microtexturing formulations, the formulation can also include an oxidant such as hydrogen peroxide, ammonium persulfate, or other appropriate oxidizing agent. In other embodiments, such as nanotexturing formulations, the formulation can be substantially free of an oxidant. Formulations can also include other components, such as chlorine-containing salts or other agents.

In some instances, the substrate surface can be exposed to a formulation for a period of time sufficient to create a desired modification (e.g., average opening size and/or average depth). In some embodiments, the exposure of any single formulation is less than about 24 hours, or less than about 12 hours, or less than about 6 hours, or less than about 2 hours, or less than about 1 hour. The exposure time can be greater than about 2 minutes or greater than about 5 minutes. In some particular embodiments, e.g., use of microtexturing formulations, the exposure period can be longer than about 2 minutes or about 5 minutes, and shorter than about 1 hour or about 2 hours. In other particular embodiments, e.g., use of nanotexturing formulations, the exposure period can be longer than about 5 minutes or about 3.5 hours, and shorter than about 24 hours.

In some embodiments, the formulation can be utilized under reasonable thermal conditions, in which the formulation can be stable (i.e., not susceptible to combustion). For instance, the formulation can be used at a temperature greater than about 10° C. but less than about 30° C., 40° C., 50° C., 60° C., 70° C., or 80° C. For example, the formulation is kept at a temperature between about 15° C. and about 30° C., or between about 20° C. and about 40° C., during exposure.

While some embodiments are directed to modifying the surface of a substrate, some processes can include the further step of treating the modified substrate with a formulation to add a calcium phosphate containing material to the modified surface 330, for example in the form of a layer contacting the surface.

Deposition of the calcium phosphate containing material can be performed in a variety of manners. In some embodiments, this can be performed by contacting the modified surface with a fluid-based calcium phosphate containing material such as a calcium phosphate containing solution. Fluid-based calcium phosphate containing compositions can include a number of components such as mineralization ions (e.g., calcium, phosphates, carbonates, magnesium, sodium, potassium, chlorine, sulfates, and silicates). In some embodiment, the deposited solid includes an ion distribution consistent with a biological composition, i.e., the calcium phosphate containing material is biomimetic.

In some instances, a calcium-phosphate solution, which can be in a metastable state, e.g., slightly acidified, to promote the precipitation of a calcium-phosphate containing solid (e.g., hydroxyapatite) on the modified surface. Some examples of calcium-phosphate containing material deposition techniques are described in U.S. Pat. No. 6,569,489, entitled "Bioactive Ceramic Coating and Method." Other potential calcium-phosphate containing material forming techniques are described in U.S. Pat. No. 6,069,295, entitled "Implant Material;" U.S. Pat. No. 6,146,686, entitled "Implant Material and Process for Using It;" and U.S. Pat. No. 6,344,061, entitled "Device for Incorporation and Release of Biologically Active Agents." Each of the patents listed in this paragraph are hereby incorporated herein by reference in their entirety.

Use of a fluid-based technique for forming a calcium phosphate containing layer on a modified surface can yield potential advantages. For example, plasma spraying techniques are a line-of-sight technology that can only deposit a calcium phosphate containing material to an exposed region. Accordingly, when a modified surface has a porous nature, plasma spraying is not able to coat all surfaces of the porous structure since some angles are hidden. Exposing the porous structure to a fluid-based deposition material can allow 360° coverage of a porous substrate. Accordingly, the entire surface can be treated with a calcium phosphate containing material to promote bone attachment. It is understood, however, that embodiments of the invention can utilize plasma spraying techniques if desired.

As discussed to previously, embodiments disclosed herein regarding modified surfaces can substantially promote calcium phosphate material deposition, which can lead to substantially increased rates of deposition. For instance, previous techniques for forming a biomimetic hydroxyapatite layer would require about 4 to 5 days to form the desired layer. In contrast, as supported by the experiments herein, some embodiments of the present invention allow deposition to be completed in less than about 24 hours. Accordingly, these embodiments can result in a substantial timesavings.

Other chemical or deposition techniques can also be used to deposit the calcium-phosphate containing material. For instance, electrochemical methods can be utilized for deposition. In some embodiments, a potential can be applied between an electrode and a porous structure (e.g., metallic), where both structures contact a solution capable of conducting electricity. The potential can drive deposition of the calcium-phosphate-containing material from the solution onto the porous structure. Other variations of this technique can also be applied, including variations known to those skilled in the art.

EXAMPLES

The following examples are provided to illustrate some embodiments of the invention. The examples are not intended to limit the scope of any particular embodiment(s) utilized.

Example 1

Atomic Force Microscopy of Cobalt-Chromium-Molybdenum Disks

Figure 4:
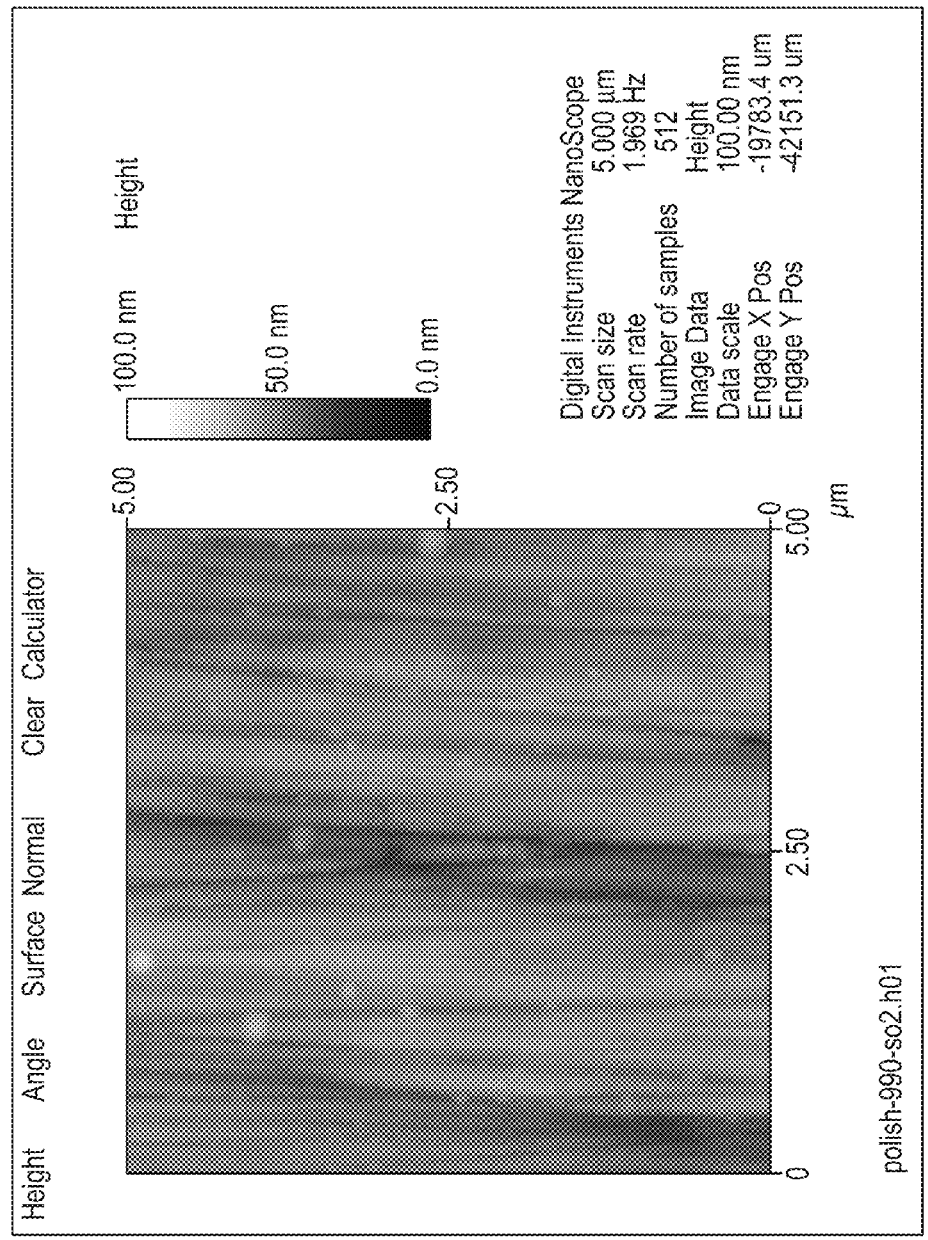
FIG. 4 presents an image from an atomic force microscope of a polished wrought cobalt-chromium-molybdenum disk, consistent with some embodiments.

An atomic force microscope (AFM) was used to perform microscopy on a number of metallic disks to characterize the surfaces of the respective samples. The images were collected using a NanoScope III using Nanoprobe™ SPM tips (RTESP14; L=125 µm). Four cobalt-chromium-molybdenum (CoCrMo) disks consistent with ASTM standard F1537 were polished according to the following procedure. Surfaces were polished using consecutively finer grit papers in the order of 180 grit, 240 grit, 320 grit, 400 grit, 600 grit, 800 grit, and 1200 grit SiC on a turning wheel (150-300 rpm) with running water. The disk was ultrasonically cleaned in RO water for 5 min, 3 min and 1 min and dried at 60° C. in an oven. AFM was performed on a 5 µm×5 µm section of one of the polished samples, yielding the image shown in FIG. 4. The image generally shows streaks from the polishing process.

Figure 5:
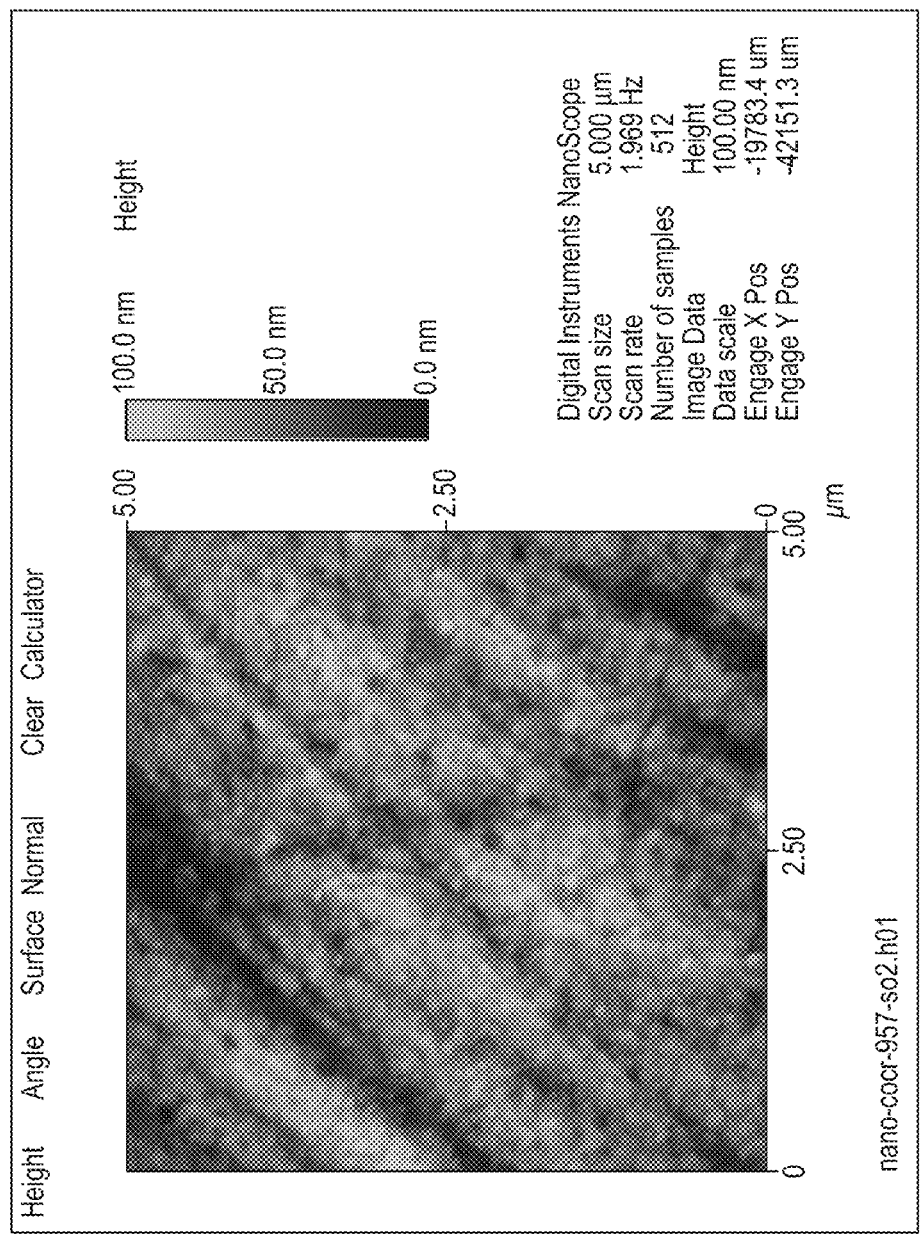
FIG. 5 presents an image from an atomic force microscope of a nanotextured wrought cobalt-chromium-molybdenum disk, consistent with some embodiments.

One surface of a polished disk was treated to provide a nanotextured surface by the following procedure. The polished disk was immersed in 30 mL of 8N HCl for 24 hours in a glass beaker at room temperature. The disk was removed from the acid after 24 hours, and consecutively rinsed and ultrasonically cleaned in reversed osmotic (RO) water for 5 min, 3 min and 1 min. The treated disk was then dried at 60° C. in an oven. AFM was performed on a 5 µm×5 µm section of the nanotextured sample, yielding the image shown in FIG. 5. The image generally shows many pit-like structures having a length scale around 100 nanometers.

Figure 6:
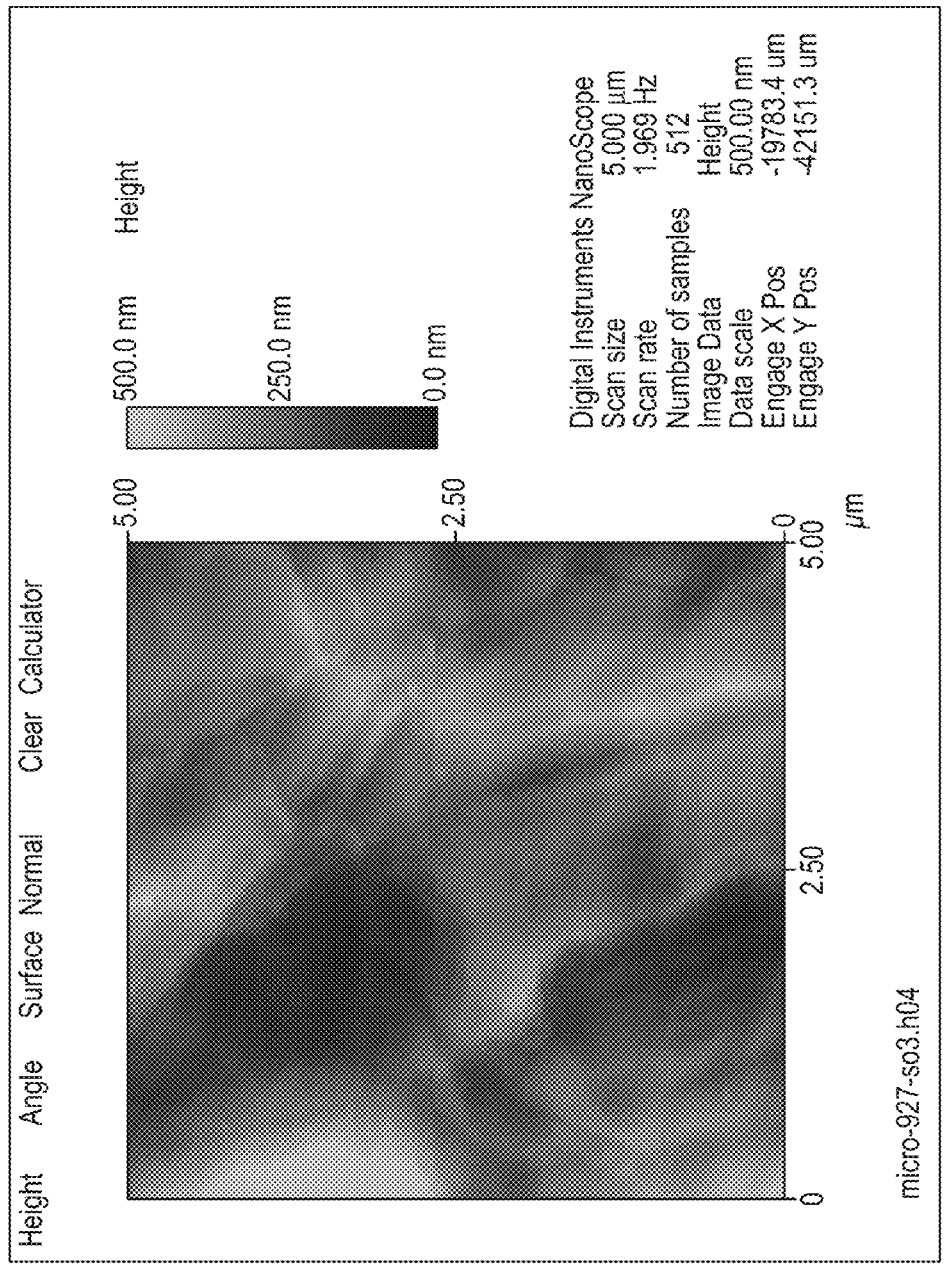
FIG. 6 presents an image from an atomic force microscope of a microtextured wrought cobalt-chromium-molybdenum disk, consistent with some embodiments.

Another polished disk was treated to provide a microtextured surface by the following procedure. The polished disk was immersed in 80 mL of 8N HCl for 30 minutes in a glass beaker. Subsequently, 20 mL of 45° C. 0.15 M ammonium persulfate was added in the beaker and the disk was removed after 60 minutes. The disk was consecutively rinsed and ultrasonically cleaned in RO water for 5 min, 3 min and 1 min, and dried at 60° C. in an oven. AFM was performed on a 5 µm×5 µm section of the microtextured sample, yielding the image shown in FIG. 6. The image shows structures much larger than found in FIG. 5, having a length scale around 1 micrometer.

Figure 7:
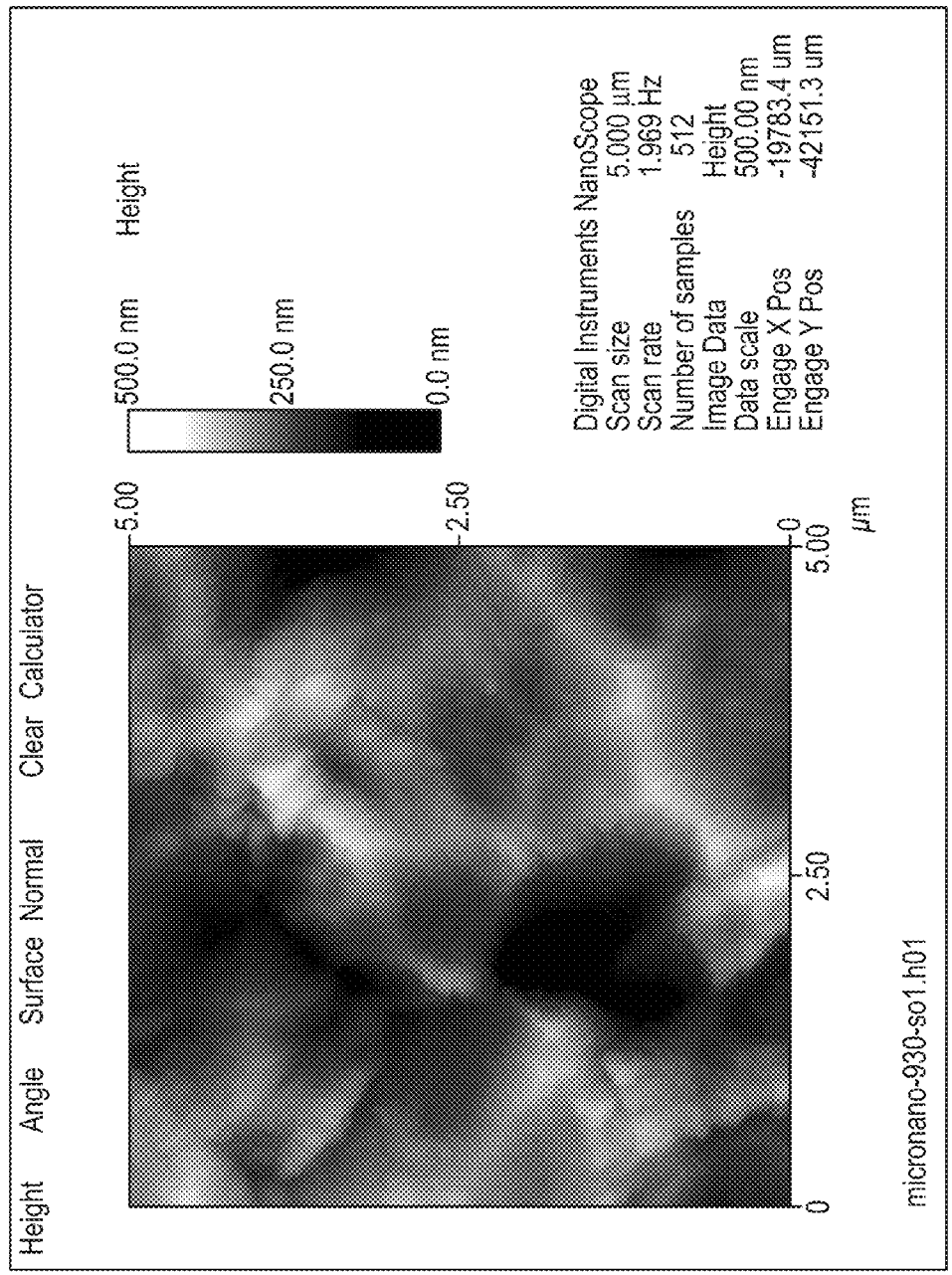
FIG. 7 presents an image from an atomic force microscope of a multitextured wrought cobalt-chromium-molybdenum disk, consistent with some embodiments.

Finally, a polished disk was treated to provide a multitextured surface by the following procedure. The polished disk was immersed in 80 mL 8N HCl for 30 minutes in a glass beaker. Subsequently, 20 mL of 45° C. 0.15 M ammonium persulfate was added in the beaker, and the disk was removed after 60 minutes. The disk was consecutively rinsed and ultrasonically cleaned in RO water for 5 min, 3 min and 1 min. The disk was further treated by immersing in 30 mL of 8N HCl at room temperature for additional 24 hours. The disk was consecutively rinsed and ultrasonically cleaned in RO water for 5 min, 3 min and 1 min and dried at 60° C. in an oven. AFM was performed on a 5 µm×5 pm section of the multitextured sample, yielding the image shown in FIG. 7. The image shows structures having a variety of length scales from around the micrometer scale down to scales smaller than 100 nanometers.

The surfaces of the samples shown in FIGS. 4-7 were also analyzed using the AFM analysis software 5.12r2 to provide measures of roughness and the area difference relative to a perfectly flat surface. These results are shown in the table below.

| Sample | Ra (nm) | Rq (nm) | Area difference (%) |
|---|---|---|---|
| polished (FIG. 4) | 6 ± 1 | 8 ± 2 | 0.8 ± 0.3 |
| nanotextured (FIG. 5) | 12 ± 2 | 15 ± 3 | 5.3 ± 1.2 |
| microtextured (FIG. 6) | 93 ± 20 | 118 ± 23 | 15.0 ± 6.6 |
| multitextured (FIG. 7) | 73 ± 23 | 96 ± 32 | 14.0 ± 8.5 |

Ra is defined by the following equation:

$$R_a = \frac{1}{L}\int_0^L \|y - Y\| dx$$

where, L is the length of the sample being measured, y is the height at a given position, and Y is the average height along the length L of the sample. Accordingly, Ra provides a measure of the average depth deviation over a given sample length. Rq is defined as:

$$R_q = \frac{1}{L}\int_0^L \sqrt{(y-Y)^2}\, dx$$

Accordingly, Rq provides a root mean square average of the depth deviations over a given sample length. The area difference is defined as:

Area difference=(measured area−theoretical flat area)/theoretical flat area where measured area represents the area measured using the AFM, and theoretical flat area represents the area scanned by the AFM if the surface were perfectly flat.

The table generally indicates that the microtexture treatment increases the surface area more than the nanotexture treatment.

Example 2

Atomic Concentration Profiles of CoCrMo Surfaces

X-ray photoelectron spectroscopy ("XPS") has been conducted on a number of CoCrMo surface samples to determine the concentration of cobalt, chromium, molybdenum, oxygen, and carbon atomic species as a function of depth from the surface. The five elements were examined (C1s, O1s, Co2p, Cr2p and Mo3d) using a pass energy of 224.00 EV and step size 0.4 EV. Using an argon ion sputter setting of 2 kv2x2, the 200 μm×200 μm (200 u45 W15 KV) areas were sputtered for a total of 2.1 minutes. The sputter cycles included 6 cycles at 0.1 min and 6 cycles at 0.2 min in Alternate Sputter Mode and have a total analysis time of 57 minutes. The relative depth of the Cr rich layer (Co depletion) is indicated by the crossing of the depth profiles of Cr and Co atomic concentration distributions as marked by the arrows in FIGS. 8-10.

Figure 8:
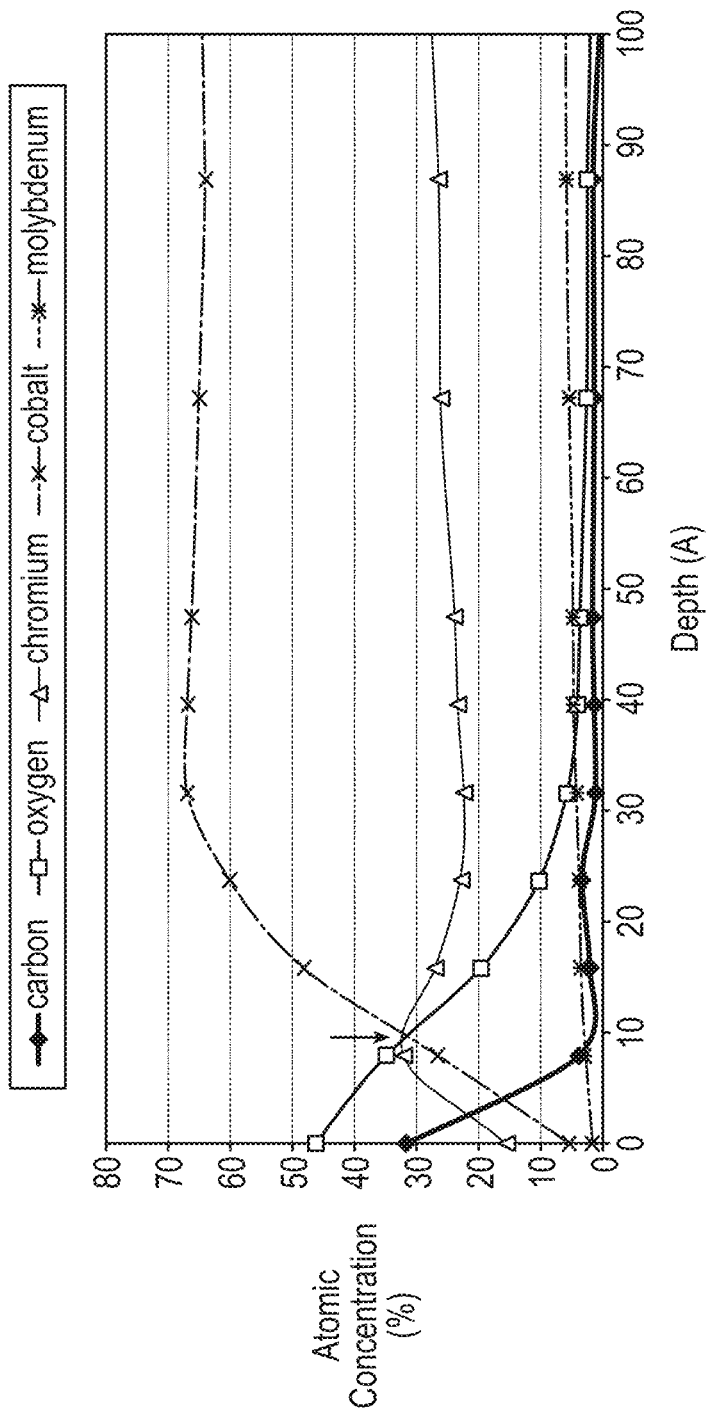
FIG. 8 presents a graph of atomic concentration versus depth for a mirror polished cobalt-chromium-molybdenum disk, in accord with some embodiments.
Figure 9:
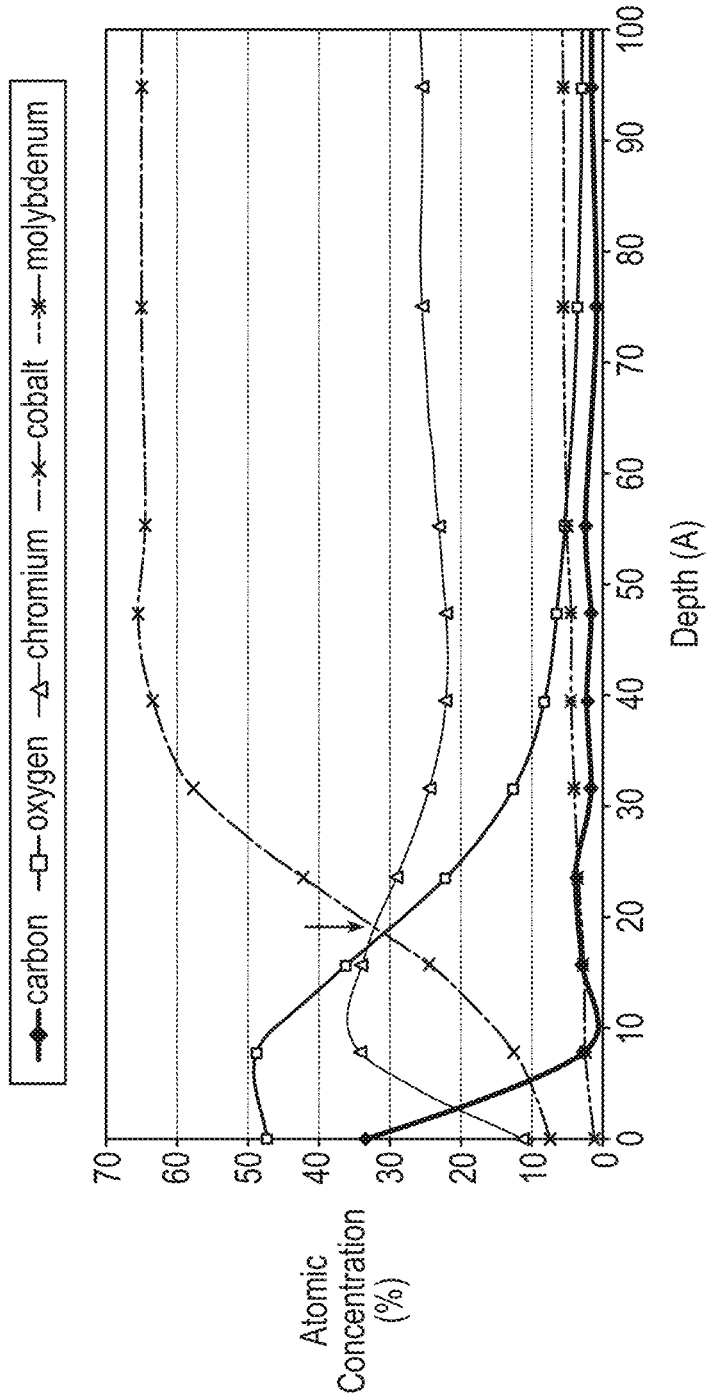
FIG. 9 presents a graph of atomic concentration versus depth for cobalt-chromium-molybdenum disk soaked in 8N HCl for about 30 minutes, in accord with some embodiments.
Figure 10:
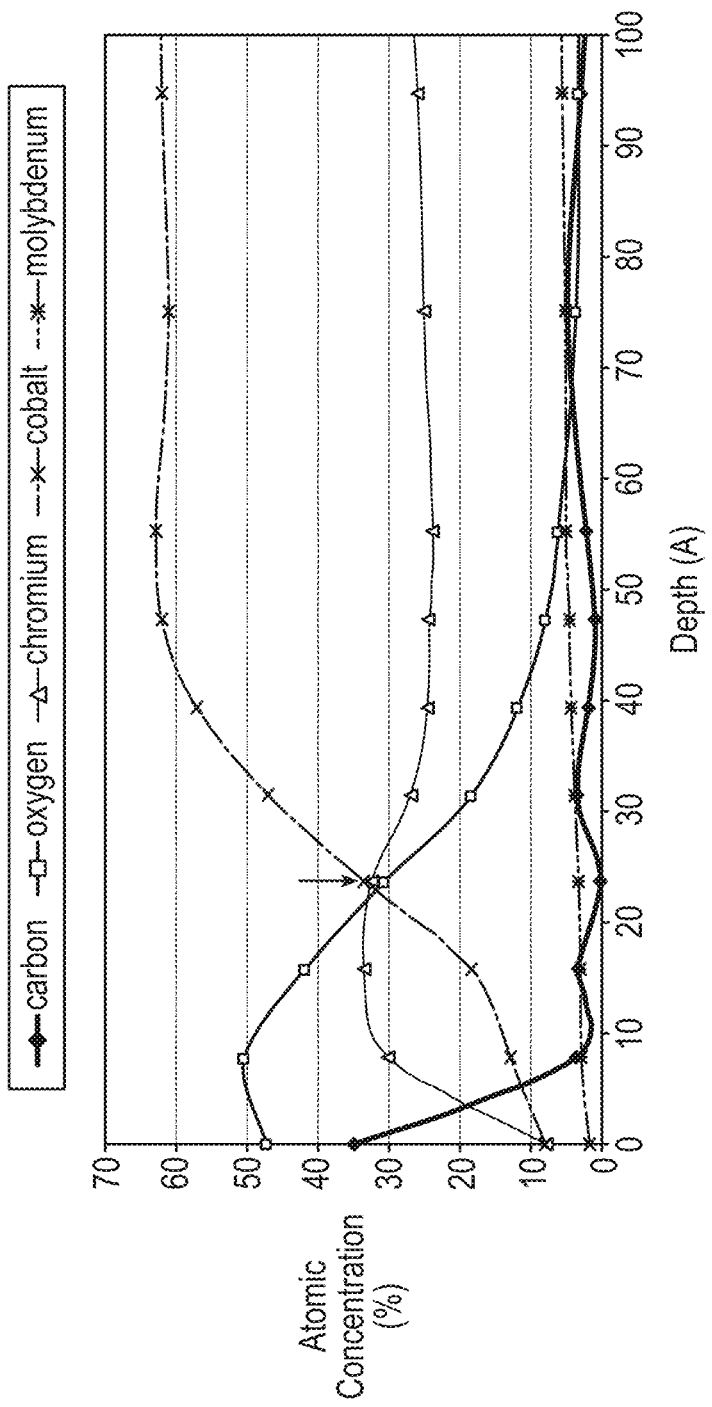
FIG. 10 presents a graph of atomic concentration versus depth for cobalt-chromium-molybdenum disk soaked in 8N HCl for about 6 hours, in accord with some embodiments.

Four cobalt-chromium-molybdenum (CoCrMo) disks consistent with ASTM standard F1537 were polished according to the following procedure. Surfaces were consecutively polished using 180 grit, 240 grit, 320 grit, 400 grit, 600 grit, 800 grit, 1200 grit SiC on a turning wheel (150-300 rpm) with running water. The disk was consecutively rinsed and ultrasonically cleaned in RO water for 5 min, 3 min and 1 min, and subsequently dried at 60° C. in an oven. FIGS. 8-10 each correspond to a particular surface types. In each of the figures, a number of profiles are graphed with each profile corresponding to one of the atomic species of carbon, oxygen, chromium, cobalt, and molybdenum as referenced in the corresponding key. FIG. 8 corresponds with XPS measurements taken from a polished sample. FIG. 9 corresponds with XPS measurements taken from a polished sample that is exposed to 8N HCl for about 30 minutes. FIG. 10 corresponds with XPS measurements taken from a polished sample that is exposed to 8N HCl for about 6 hours.

FIGS. 8-10 generally show that the total cobalt concentration close to the surface tends to decline with HCl treatments vis-à-vis the untreated polished sample. The depletion of cobalt in the near surface region results in a higher Cr/Co ratio relative to the untreated sample. For example, the Cr/Co ratio is about one at 10 angstroms for the polished surface, and the Cr/Co ratio is about three for the HCl treated surfaces.

Example 3

Degree of Hydrophobicity of CoCrMo Surfaces

Figure 11:
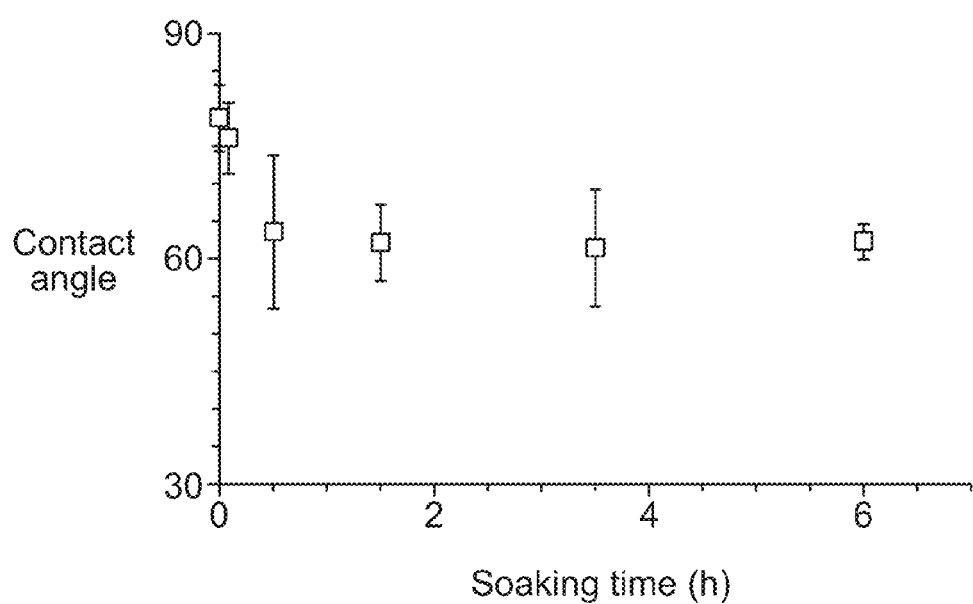
FIG. 11 presents a graph of contact angle versus soaking time in 8N HCl for samples of cobalt-chromium-molybdenum, consistent with some embodiments.

The samples corresponding to FIGS. 8-10, among others, were also tested to determine contact angles to indicate the ability for water to uniformly wet the surface. The contact angle was measured by dosing one drop of 5 μL deionized water on the ¾" wrought disk using a standard contact angle measuring instrument, and extracting the contact angle by applying the drop shape analysis. The same test was repeated in triplicate. In general, higher contact angles correlate with more hydrophobic surfaces. A graph of the measured contact angle as a function of the soaking time that the surface was exposed to 8N HCl is presented in FIG. 11. The measurements generally show that increased exposure to the formulation results in a more hydrophilic surface.

Example 4

Calcium Phosphate Loading on CoCrMo Beaded Surfaces

Nine 1 in. diameter samples of CoCrMo Porocoat disks, having CoCrMo Porocoat beads sintered thereto in vacuum, were tested. The beads on each sample were about 100 μm to about 350 μm in diameter. The bead layer on each disk was about 0.75 mm thick, and the porosity of the bead layer was about 40% to about 50%.

Three of the samples were first exposed to a formulation containing 6.4N HCl and 0.15M ammonium persulfate for about one hour, resulting in microtexturing. Three other samples were first exposed to a formulation containing 8N HCl for about 24 hours, resulting in nanotexturing. The final three samples were not exposed to an etching formulation. All nine samples were vertically oriented on a Teflon fixture, and immersed in 1 L of a coating solution for about 16 hours at about 37° C. The coating solution included NaCl (150.2 mM), $K_2HPO_4$ (2.4 mM), $MgCl_2.6H_2O$ (2.5 mM), $CaCl_2. 2H_2O$ (6 mM), Tris(hydroxymethyl)aminomethane (17.5 mM), $NaHCO_3$ (8 mM), 18 mL of 1N HCl, and water to create a total 1 L solution. The final coating solution had an initial pH of about 6.9 before samples were added. After 16 hours of the coating process, the samples were removed from the coating solution, rinsed three times in ethanol, and dried at ambient room conditions.

Figure 12C:
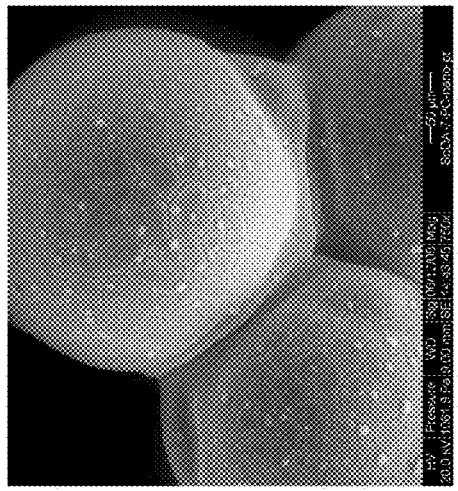
FIG. 12C presents a micrograph from a scanning electron microscope showing a nanoetched CoCrMo Porocoat beaded surface treated with a coating material to form a calcium phosphate containing layer thereon.
Figure 12B:
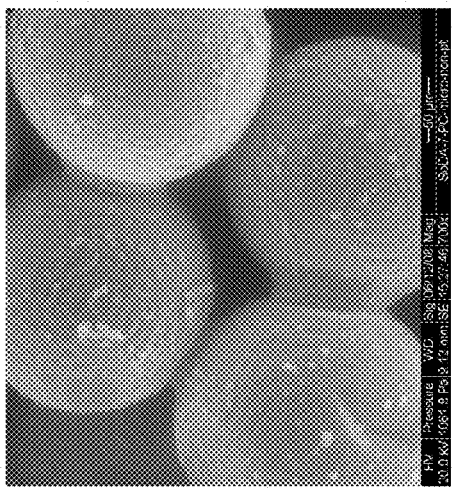
FIG. 12B presents a micrograph from a scanning electron microscope showing a microetched CoCrMo Porocoat beaded surface treated with a coating material to form a calcium phosphate containing layer thereon.
Figure 12A:
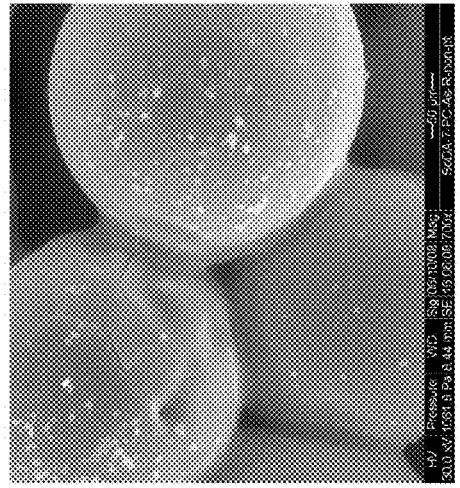
FIG. 12A presents a micrograph from a scanning electron microscope showing an unetched CoCrMo Porocoat beaded surface treated with a coating material to form a calcium phosphate containing layer thereon.

Representative scanning electron micrographs of coated samples that were originally unetched, etched with HCl and ammonium persulfate, and etched with only HCl, are shown in FIGS. 12A, 12B, and 12C, respectively. The crackings in the micrographs are believed to be the result of water evaporation in vacuum drying.

The weight of each sample was recorded before immersion in the coating solution and after drying. Accordingly, the weight of calcium-phosphate containing material deposited per projected area of the disk, 0.79 in$^2$, was calculated for each sample. For each condition of unetched, microetched, and nanoetched, an aerial loading density and the corresponding standard deviation were calculated. The results are shown in the table below.

| Sample | Average CaP Loading (mg/in$^2$) | Standard Deviation (mg/in$^2$) |
|---|---|---|
| unetched | 3.92 | 0.28 |
| microetched | 6.93 | 0.76 |
| nanoetched | 7.35 | 0.68 |

In general, the nanotextured samples have the highest loadings of calcium phosphate containing materials while the unetched samples exhibit the lowest loadings of calcium phosphate containing materials.

Example 5

Calcium Phosphate Loading on Grit Blasted CoCrMo Surfaces

Six samples of polished wrought CoCrMo (ASTM F1537) disks, having 1 in. diameters, were grit-blasted using 50:50 ratio of alumina (60 grit) and glass beads (60 grit). Three of the samples were etched in 8N HCl for about 24 hours, to yield an acid etched surface. The remaining three samples were not exposed to an etching formulation. All samples were inserted in a teflon fixture so that the grit-blasted surfaces stood vertically in a calcium-phosphate coating solution as recited in Example 4. Immersion in the 1 L coating solution lasted about 16 hours at about 37° C. The final coated samples were rinsed three times in ethanol and dried in room condition.

Figure 13A:
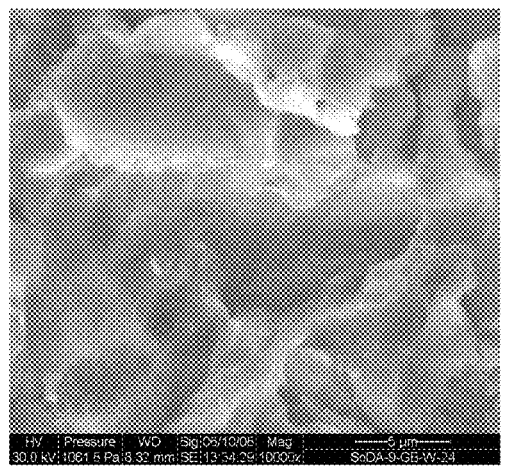
FIG. 13A presents a micrograph from a scanning electron microscope showing a grit-blasted CoCrMo surface coated with a calcium phosphate containing layer.
Figure 13B:
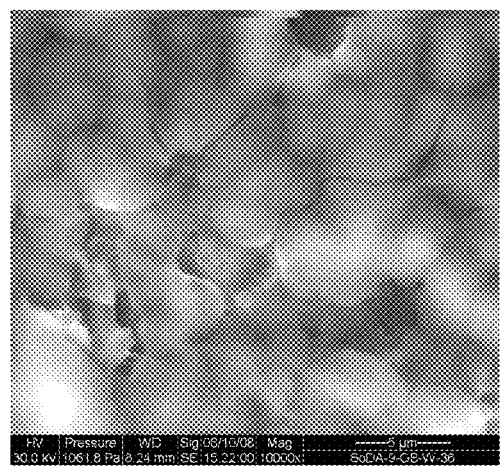
FIG. 13B presents a micrograph from a scanning electron microscope showing a grit-blasted and nanoetched CoCrMo surface coated with a calcium phosphate containing layer.

Representative scanning electron micrographs of coated samples that were only grit blasted, and grit blasted and etched with HCl are shown in FIGS. 13A and 13B, respectively.

The weight of each sample was recorded before immersion in the coating solution and after drying. Accordingly, the weight of calcium-phosphate containing material deposited per projected area of the disk, 0.79 in$^2$, was calculated for each sample. For each condition of only grit blasting and grit blasted followed by etching, an aerial loading density and the corresponding standard deviation were calculated. The results are shown in the table below.

| Sample | Average CaP Loading (mg/in$^2$) | Standard Deviation (mg/in$^2$) |
|---|---|---|
| Grit blast (GB) | 0.96 | 0.71 |
| GB + nanoetched | 2.57 | 0.59 |

In general, the grit blasted and nanoetched surfaces have substantially higher coating masses than the surfaces that are only grit blasted.

Example 6

Comparative Calcium Phosphate Loading on CoCrMo Beaded Surfaces

Forty 1 in. diameter samples of CoCrMo Porocoat disks, having CoCrMo Porocoat beads sintered thereto in vacuum, were tested. The beads on each sample were about 150 μm to about 250 μm in diameter. The bead layer on each disk was about 0.75 mm thick Seventeen of the samples were first exposed to a formulation containing 6.4N HCl and 0.15M ammonium persulfate for about one hour, resulting in microtexturing. Six other samples were first exposed to a formulation containing 8N HCl for about 24 hours, resulting in nanotexturing. Six samples were subjected to a dual texturing process by processing the samples using the HCl and ammonium persulfate treatment described above followed by HCl only treatment described above. The remaining eleven samples were not exposed to an etching formulation. All forty samples were vertically oriented on a Teflon fixture, and immersed in a calcium phosphate coating solution as described in Example 4 for about 16 hours at about 37° C. The samples were then removed from the coating solution, rinsed three times in ethanol, and dried at ambient room conditions.

The weight of each sample was recorded before immersion in the coating solution and after drying. Accordingly, the weight of calcium-phosphate containing material deposited per projected area of the disk was calculated for each sample. For each condition of unetched, microetched, nanoetched, and multietched, an aerial loading density and the corresponding standard deviation were calculated. The results are shown in the table below.

| Sample | Average CaP Loading (mg/in$^2$) | Standard Deviation (mg/in$^2$) |
|---|---|---|
| unetched | 2.9 | 1.4 |
| microetched | 6.2 | 1.4 |
| nanoetched | 6.4 | 0.9 |
| multietched | 8.7 | 1.3 |

In general, the multitextured samples have the highest loadings of calcium phosphate containing materials, followed by the nanotextured samples. The unetched samples exhibit the lowest loadings of calcium phosphate containing materials.

EQUIVALENTS

While the present invention has been described in terms of specific methods, structures, and devices it is understood that variations and modifications will occur to those skilled in the art upon consideration of the present invention. For example, the methods and compositions discussed herein can be utilized beyond the preparation of metallic surfaces for implants in some embodiments. As well, the features illustrated or described in connection with one embodiment can be combined with the features of other embodiments. Such modifications and variations are intended to be included within the scope of the present invention. Those skilled in the art will appreciate, or be able to ascertain using no more than routine experimentation, further features and advantages of the invention based on the above-described embodiments. Accordingly, the invention is not to be limited by what has been particularly shown and described, except as indicated by the appended claims.

All publications and references are herein expressly incorporated by reference in their entirety. The terms "a" and "an" can be used interchangeably, and are equivalent to the phrase "one or more" as utilized in the present application. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. A method for preparing a surface of an implant, comprising:
   exposing a metallic substrate to a first formulation to form a first chemically modified, texturized surface on the metallic substrate, the first texturized surface characterized by a first plurality of surface pits exhibiting a first average opening size in a range from about 200 nanometers to about 10 micrometers; and
   exposing the metallic substrate to a second formulation to form a second chemically modified, texturized surface on the metallic substrate, the second texturized surface characterized by a second plurality of surface pits exhibiting a second average opening size in a range from about 40 nanometers to about 200 nanometers,
   the surface capable of enhancing calcium phosphate formation on the surface relative to exposing the surface to only one of the first and second formulations
   wherein the metallic substrate comprises a cobalt-chromium alloy;
   wherein the surface after the exposing steps exhibits a layer having an enhanced chromium to cobalt ratio in at least a portion of the layer relative to a cobalt-chromium alloy not undergoing the exposing steps, the layer having a thickness less than about 25 angstroms.

2. The method of claim 1, further comprising:
   treating the metallic substrate with a third formulation to form a calcium phosphate containing layer on the first and second texturized surfaces.

3. The method of claim 2, wherein the step of treating the metallic substrate comprises forming a hydroxyapatite-containing layer.

4. The method of claim 2, wherein the step of treating the metallic substrate comprises treating the metallic substrate for a time period less than about 24 hours.

5. The method of claim 1, wherein the step of exposing the metallic substrate to the first formulation is performed before the step of exposing the metallic substrate to the second formulation.

6. The method of claim 1, wherein the first formulation comprises a first hydrohalic acid and an oxidant.

7. The method of claim 1, wherein the second formulation comprises a second hydrohalic acid, the second formulation being substantially free of an oxidant.

8. The method of claim 1, further comprising:
   mechanically roughening a surface of the metallic substrate before the steps of exposing the metallic substrate.

9. The method of claim 1, further comprising:
   subjecting the metallic substrate to a plasma followed by the steps of exposing the metallic substrate.

10. The method of claim 1, wherein the first plurality of surface pits exhibits a first average depth size in a range from about 50 nm to about 500 nm.

11. The method of claim 1, wherein the second plurality of surface pits exhibits a second average depth size in a range from about 5 nm to about 50 nm.

12. The method of claim 1, wherein the step of exposing the metallic substrate to the first formulation comprises exposing the metallic substrate for a time period in a range from about 2 minutes to about 120 minutes.

13. The method of claim 1, wherein the step of exposing the metallic substrate to the second formulation comprises exposing the metallic substrate for a time period of at least about 5 minutes.

14. The method of claim 1, wherein the metallic substrate further comprises a titanium alloy.

15. A method for improving calcium phosphate coating of an implant, comprising:
   exposing a metallic substrate comprising a cobalt-chromium alloy surface to a first formulation to impart a chemically modified, texturized surface to the metallic substrate, the texturized surface characterized by a plurality of surface pits exhibiting an average opening size in a range from about 40 nanometers to about 10 micrometers; and
   treating the texturized surface with a second formulation to form a calcium phosphate containing layer on the texturized surface, the texturized surface enhancing calcium phosphate formation on the metallic substrate;
   wherein the surface of the metallic substrate, following the exposing step, exhibits a layer having an enhanced chromium to cobalt ratio in at least a portion of the layer relative to a cobalt-chromium alloy not undergoing the exposing step.

16. The method of claim 15, wherein the metallic substrate comprises a porous structure, the texturized surface being at least a portion of a surface of the porous structure.

17. The method of claim 15, wherein the first formulation comprises a hydrohalic acid and an oxidant.

18. The method of claim 15, wherein the first formulation comprises a hydrohalic acid, the first formulation being substantially free of an oxidant.

19. The method of claim 15, wherein the step of treating the metallic substrate comprises treating the metallic substrate for a time period in a range from about 2 minutes to about 24 hours.

* * * * *